(12) United States Patent
Geneste et al.

(10) Patent No.: US 7,459,434 B2
(45) Date of Patent: Dec. 2, 2008

(54) PEPTIDE INTERACTING WITH ANTI-APOPTOTIC PROTEINS OF THE BCL-2 FAMILY

(75) Inventors: Olivier Geneste, Rueil-Malmaison (FR); John Hickman, Paris (FR); Richard Bennett, Paris (FR); Jean-Christophe Rain, Ermont (FR)

(73) Assignee: Les Laboratories Servier, Courbevoie Cedex (FR)

( * ) Notice: Subject to any disclaimer, the term of this patent is extended or adjusted under 35 U.S.C. 154(b) by 0 days.

(21) Appl. No.: 10/566,668

(22) PCT Filed: Aug. 4, 2004

(86) PCT No.: PCT/FR2004/002081

§ 371 (c)(1),
(2), (4) Date: Jan. 31, 2006

(87) PCT Pub. No.: WO2005/014638

PCT Pub. Date: Feb. 17, 2005

(65) Prior Publication Data

US 2006/0183688 A1    Aug. 17, 2006

(30) Foreign Application Priority Data

Aug. 6, 2003   (FR) .................................. 03 09697

(51) Int. Cl.
*A61K 38/00*   (2006.01)
*C12N 15/00*  (2006.01)
*C12N 1/20*   (2006.01)
*C07H 21/04*  (2006.01)

(52) U.S. Cl. ................. 514/12; 530/350; 536/23.1; 435/252.3; 435/320.1

(58) Field of Classification Search ................. 530/350; 435/69.1, 252.3, 320.1; 514/12; 536/23.1
See application file for complete search history.
M

(56) References Cited

U.S. PATENT DOCUMENTS 5,283,173 A    2/1994  Fields et al.
2003/0032157 A1*  2/2003  Hammond et al. .......... 435/184

FOREIGN PATENT DOCUMENTS

WO    WO 02072761    9/2002

OTHER PUBLICATIONS

Shimkets et al., Geneseq Database, Accession No. AAC74541, Feb. 2001.*
International Preliminary Examination Report for PCT/FR2004/002081 of Jul. 13, 2006.
Cory, et al., Nature Reviews Cancer, 2002, 2:647-656.
Slade, et al., Genbank Accession No. ABJ18850, available online Oct. 8, 2006.
Kelekar, et al., Trends In Cell Biology, 1998, 8L324-330.
Degterev, et al., Nature Cell Biology, 2001, 3:173-182.
International Search Report for PCTFR2004/002081, Jan. 14, 2005.

* cited by examiner

*Primary Examiner*—Maryam Monshipouri
(74) *Attorney, Agent, or Firm*—Hueschen and Sage

(57) ABSTRACT

The invention relates to the identification of a new peptide interacting with the anti-apoptotic proteins Bcl-2, Bcl-W and/or Bcl-XL, and also to screening methods allowing identification of modifiers of those interactions.

15 Claims, 3 Drawing Sheets

*Figure 1*: "GST pull-down" GST-Bcl-XL + TBid with competition by the peptide described in SEQ. ID. NO.1
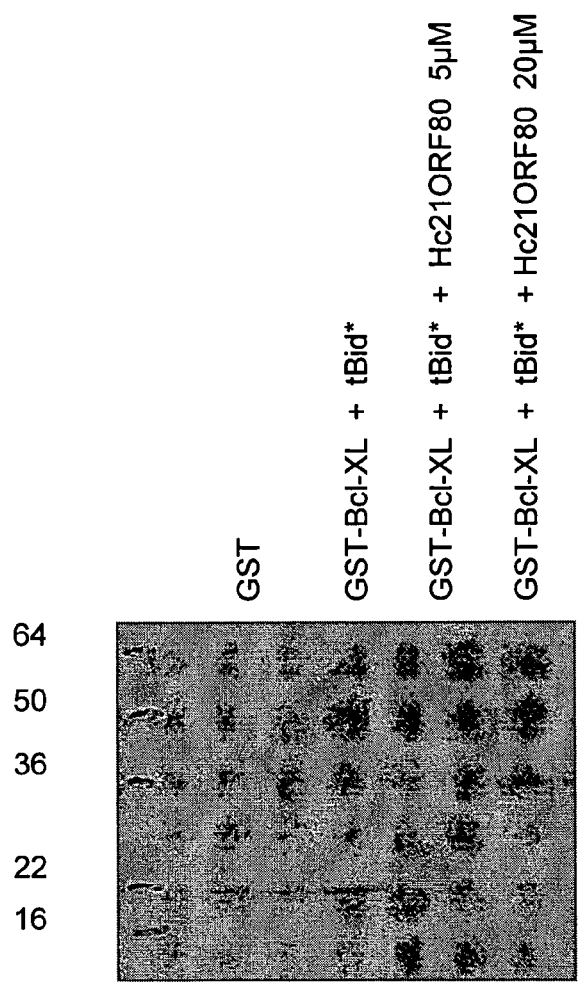

*Figure 2* : *Determination of the $K_d$ of the peptide described in SEQ. ID. NO.1 for Bcl-XL*
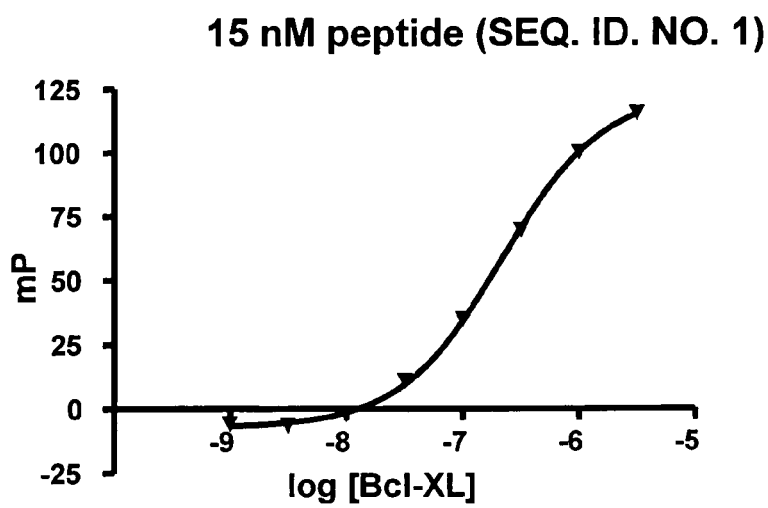
$K_d = 2.15 \times 10^{-7} M$

*Figure 3* : *Determination of the $K_d$ of the peptide described in SEQ. ID. NO.1 for Bcl-W*
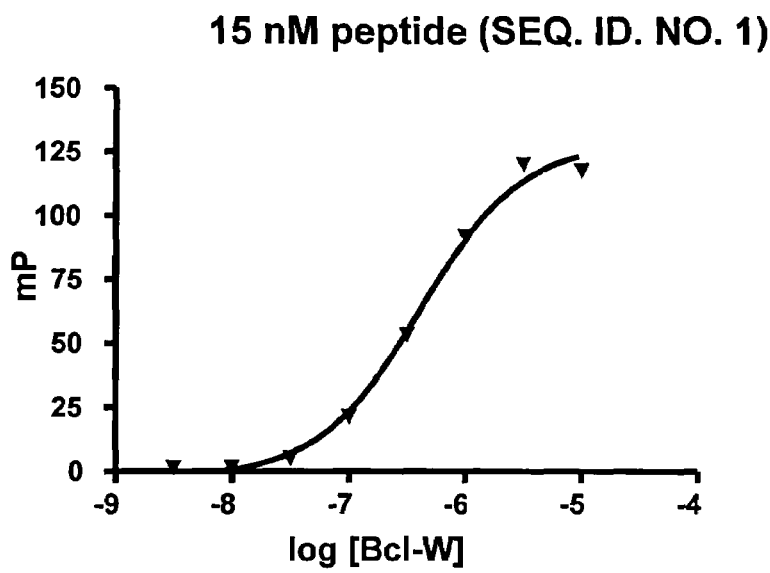
$K_d = 4.11 \times 10^{-7} M$

PEPTIDE INTERACTING WITH ANTI-APOPTOTIC PROTEINS OF THE BCL-2 FAMILY

This application is a 371 of PCT/FR04/02081, filed Aug. 4, 2004, which claims priority to French patent application 030697 filed Aug. 6, 2003.

The present invention relates to a new peptide interacting with Bcl-XL and/or Bcl-2 and/or Bcl-W, and also to screening methods allowing identification of compounds that are capable of modifying that interaction.

Most biological processes involve protein-protein interactions. One of the goals set by proteomics is to produce a map of those interactions. By virtue of their being involved in most signal transduction mechanisms, these interactions are targets of choice in the development of a medicament.

There are numerous methodologies which allow protein interactions to be identified. One of the most widespread is the two-hybrid system initially developed and described by Fields et al. (U.S. Pat. Nos. 5,283,173; 5,468,614; 5,667,973).

This system basically consists of an in vitro test between two recombined proteins. The first of these, known as the "bait" protein, is a chimeric protein fused to a DNA binding domain (BD) capable of binding upstream of a reporter gene. The binding domains commonly used are those of Gal4 or *E. coli* LexA.

The second protein is also a chimeric protein, commonly known as the "prey", which contains an activation domain (AD), generally coming from Gal4.

However, those conventional methods have their limitations. It is well known, for example, that such screening methods can result in false positives and/or false negatives, and biochemical confirmations of the results obtained are necessary.

A more effective technique allowing false positives or negatives to be minimised is described in the patent application WO9942612 and uses recombinant haploid yeasts containing the "bait" and "prey" proteins. This system allows detection of a greater number of "preys" using one "bait" in a more precise, more reproducible and more sensitive manner than the other conventional methods used in the field.

Apoptosis is a process of cell death that plays a crucial role in multicellular organisms. There are, in fact, two forms of cell death: necrosis and apoptosis. Necrosis is found in the case of tissue lesions: the cells swell, leading to release of the cellular contents and then to lysis of the cell, causing inflammation of the surrounding tissues.

Apoptosis, on the other hand, is a physiological process which is programmed and regulated and the importance of which cannot be underestimated because about $10^9$ of our cells die by this mechanism every day. Numerous pathologies are linked to deregulation of the equilibrium that exists between cell growth, survival and death.

There may be mentioned, in particular, autoimmune diseases, certain neurological disorders and cancers.

Keeping a cell alive or programming its death requires at least ten families of different proteins, among which the Bcl-2 family plays a major role. This family comprises about twenty proteins, including Bcl-2, Bcl-XL and Bcl-W, which are anti-apoptotic proteins favouring survival of the cell, as opposed to Bax, Bak and Bid, which are pro-apoptotic proteins. In the course of apoptosis it would seem that the members of the Bcl-2 family modify their interactions with their partners so as to cause irreversible changes in the cell leading to cell death.

It is accordingly essential to be able to identify compounds capable of modifying those interactions in order to obtain real candidate medicaments that are efficacious in pathologies involving deregulation of apoptosis, especially autoimmune diseases, certain neurodegenerative disorders and cancers.

The Applicants have now identified a new peptide interacting with anti-apoptotic proteins of the Bcl-2 family, more especially Bcl-2, Bcl-XL and Bcl-W.

This peptide of 22 amino acids corresponds to the precise interaction domain with anti-apoptotic proteins of the Bcl-2 family, more especially Bcl-2 and/or Bcl-XL and/or Bcl-W, and has the typical structural features of a "BH3" motif, the interaction domain allowing the formation of homo- or hetero-dimers.

The small size of this peptide makes it an ideal candidate for developing a test allowing highly efficient screening of compounds that are capable of modifying interactions between those proteins.

Numerous tests are found in the literature for screening modifiers of protein-protein interactions but they often have limitations with regard to their sensitivity and their high-throughput feasibility. The methods customarily employed necessitate the use of complex tools (interactions between fusion proteins, between recombinant proteins etc.), which is not very compatible with high-throughput screening. Very frequently they generate a high level of background noise and are of low reliability from a quantitative point of view: they provide a reduced reading window that does not allow optimum screening of the compounds tested.

However, the Applicants have developed a highly efficient screening test based on fluorescence polarisation (Owicki J. C. et al., Journal of Biomolecular Screening, 5, 2000, 297-306). This technique allows, for example, measurement of the interaction between a fluorophore-labelled ligand and a receptor. The principle consists of measuring an increase in the polarisation of fluorescence emitted by the ligand when bound to its receptor compared to that emitted by the free ligand. The fluorescence polarisation of the free ligand is dependent on its molecular weight and will be greater the higher the molecular weight of the aforesaid ligand. Accordingly, when this test is carried out using a ligand of high molecular weight, having a high level of intrinsic fluorescence polarisation, it will be difficult to reliably evaluate the difference in fluorescence polarisation between the free ligand and the bound ligand. Using a ligand of reduced size, on the other hand, will allow that difference to be accentuated and consequently allow the precision of the assay to be increased. It will accordingly be possible to better evaluate the real activity of a compound and to carry out high-throughput screenings.

More specifically, the present invention relates to the peptide comprising the sequence of amino acids described in SEQ. ID. NO.1 and to its functional variants.

"Functional variants" are understood to be any fragments or point mutants of the peptide described in SEQ. ID. NO.1 that are capable of interacting with anti-apoptotic proteins of the Bcl-2 family, more especially Bcl-2 and/or Bcl-XL and/or Bcl-W.

This peptide was identified by the two-hybrid method using Bcl-XL, Bcl-W and Bcl-2 as "bait" proteins. Three banks of human cDNA (placenta, brain, cell line CEMC7) were screened and allowed the identification of "prey" fragments corresponding to partial sequences of the sequence HC21ORF80 (Accession Number NM_015227).

It was then determined experimentally by the two-hybrid technique that a fragment of that sequence is necessary and sufficient to obtain the interaction with Bcl-XL and/or Bcl-2 and/or Bcl-W and corresponds to the fragment of 22 amino acids described in SEQ. ID. NO.1.

Interaction with the proteins Bcl-2, Bcl-W and Bcl-XL was validated by biochemical techniques (co-immunoprecipitation, GST pull-down), and it was possible to confirm the biological activity of this peptide by transfections and/or microinjections into cells where it was shown to cause apoptosis.

The present invention relates also to sequences of nucleic acids deduced according to the genetic code from the sequence of amino acids described in SEQ. ID. NO.1, and also to those deduced from the functional variants described hereinbefore.

More specifically, the invention relates to the nucleic acid sequence SEQ. ID. NO.2 coding for the peptide described in SEQ. ID. NO.1.

A "nucleic acid sequence" is to be understood as a nucleic acid sequence isolated from its natural context and in particular denotes sequences that have been isolated, amplified and/or purified and, as the case may, modified by genetic engineering.

The invention relates also to a recombinant vector comprising a nucleic acid sequence according to the invention.

A "vector" is to be understood as any type of vector allowing introduction of the nucleic acid sequence into a host cell and expression of the polypeptide.

The recombinant vector according to the invention is characterised in that it comprises DNA sequences necessary for expression of the peptides according to the invention and, more especially, of the peptide described in SEQ. ID. NO.1.

There may be mentioned, in particular, vectors derived from bacterial plasmids, bacteriophages, yeast plasmids and chromosomes, viruses etc.

The invention relates also to host cells transformed by the recombinant vectors. These cells are preferably bacteria or eukaryotic cells. There may be mentioned, by way of example, *Escherichia coli*, yeasts, insect cells or mammalian cells.

The invention relates furthermore to a method of screening agents capable of modifying the interaction between the peptides according to the invention, more especially the peptide described in SEQ. ID. NO.1, and anti-apoptotic proteins of the Bcl-2 family, more especially Bcl-2, Bcl-W and Bcl-XL. The agents modifying those interactions will advantageously be compounds that have been chemically synthesised or obtained from compound banks.

The screening method according to the invention comprises the following steps:
a) preparation of a peptide according to the invention labelled with a fluorescent label;
b) incubation with the compound under test;
c) addition of the fusion protein comprising the anti-apoptotic protein;
d) measurement of the fluorescence polarisation.

The invention relates especially to the method of screening compounds capable of inhibiting the interaction between the peptide and the anti-apoptotic protein, comprising the following steps:
a) preparation of the peptide according to the invention labelled with a fluorescent label;
b) incubation with the compound under test, or not;
c) addition of the fusion protein comprising the anti-apoptotic protein;
d) measurement of the fluorescence polarisation with and without the compound under test;
e) selection of the compounds for which the increase in fluorescence polarisation observed with the compound under test is significantly less than that observed without the compound under test.

The invention relates especially to the method of screening compounds capable of enhancing the interaction between the peptide and the anti-apoptotic protein, comprising the following steps:
a) preparation of the peptide according to the invention labelled with a fluorescent label;
b) incubation with the compound under test, or not;
c) addition of the fusion protein comprising the anti-apoptotic protein;
d) measurement of the fluorescence polarisation with and without the compound under test;
e) selection of the compounds for which the increase in fluorescence polarisation observed with the compound under test is significantly greater than that observed without the compound under test.

According to a preferred embodiment of the methods described hereinbefore, the fluorescent label will be, for example, Oregon Green, Bodipy or fluorescein, more especially fluorescein.

The peptide according to the invention used in the screening methods will preferably be the peptide described in SEQ. ID. NO.1.

The methods according to the invention will advantageously be carried out using anti-apoptotic proteins of the Bcl-2 family, more especially Bcl-2, Bcl-W and Bcl-XL.

Consequently, the invention relates also to use of the peptides according to the invention in the screening, according to the methods of the invention, of active compounds capable of modifying apoptosis.

More specifically, the invention relates to use of the peptides according to the invention in the screening, according to the methods of the invention, of compounds that are useful in the treatment of pathologies involving deregulation of apoptosis.

The invention accordingly relates to use of the peptides according to the invention in the screening, according to the methods of the invention, of compounds that are useful in the treatment of autoimmune diseases, certain neurological disorders and cancers.

DESCRIPTION OF THE FIGURES

FIG. 1: "GST pull-down" GST-Bcl-XL+TBid with competition by the peptide described in SEQ. ID. NO.1.

FIG. 2: Determination of the $K_d$ of the peptide described in SEQ. ID. NO.1 for Bcl-XL FIG. 3: Determination of the $K_d$ of the peptide described in SEQ. ID. NO.1 for Bcl-W The following Examples illustrate the invention without limiting it in any way:

EXAMPLE 1

Identification of the Peptide Described in SEQ. ID. NO.1

Three banks of human cDNA (placenta, brain, cell line CEMC7) were screened by the two-hybrid technique (Fields et al.) in yeast using the conjugation protocol (Legrain et al., Nature Genetics, 1997, 16, 277-282).
1) Preparation of "Baits" and "Preys"
a) The "baits" used are:
C-terminal truncate of Bcl-XL (1-209) fused to the LexA DNA binding domain
C-terminal truncate of Bcl-2 (1-211) fused to the LexA DNA binding domain.

They are expressed in *Saccharomyces cerevisiae* (CG1945 or L40ΔGal4) and precultured at 30° C. in a synthetic medium lacking tryptophan (DO-Trp) until a $DO_{600\,nm}$ of between 0.1 and 0.5 inclusive is obtained. Fifty ml of a dilution of that preculture ($DO_{600\,nm}$=0.006) are incubated at 30° C. overnight.

b) A collection of yeasts containing the plasmids expressing the cDNA banks, fused to the Gal4 transcription activation domain, is obtained by transformation following selection on a medium lacking leucine (DO-Leu). The yeasts are divided into aliquots and stored at −80° C.

2) Conjugation

Conjugation is carried out using a "bait"/"prey" ratio of 2.

An amount of "yeast bait" cells obtained in Step 1)a) corresponding to 50 units of $DO_{600\,nm}$ is mixed with the "yeast preys" obtained in Step 1)b). After centrifugation, the sediment is resuspended in a YPGlu medium, spread onto YPGlu culture plates and incubated for 4 hours 30 minutes at 30° C. Selection of the conjugated yeasts containing a "bait" and a "prey" capable of interacting with one another is carried out in a DO-Leu-Trp-His medium: the absence of leucine and tryptophan makes it possible to maintain a selection pressure allowing only those yeasts that contain the two types of plasmid ("baits"/"preys") to develop; the absence of histidine from the medium makes it possible to select the conjugated yeasts containing a "bait" plasmid and a "prey" plasmid capable of interacting with one another: this interaction makes it possible to activate the HIS3 gene, which codes for an enzyme involved in the biosynthesis of histidine.

3) Identification of Positive Clones

The "prey" fragments of a colony of yeasts selected according to 2) are amplified by PCR starting from a crude lysate of that colony using specific primers of the "prey" vector:

```
ABS1 5'-GCTTTGGAATCACTACAGG-3', (SEQ. ID. NO. 3)

ABS2 5'-CACGATGCACGTTGAAGTG-3'. (SEQ. ID. NO. 4)
```

The PCR products are then sequenced and the sequences obtained are identified by comparison with databases.

Among the positive clones obtained, it was possible to identify fragments of about 300 amino acids as being partial sequences of the sequence HC21ORF80 (Accession Number: NM_015227).

4) Identification of the Peptide Described in SEQ. ID. NO.1

Two-hybrid experiments carried out according to Steps 1), 2) and 3) described above on smaller fragments of the sequence HC21ORF80 allowed identification of a short peptide of 22 amino acids as being necessary and sufficient to obtain the interaction with Bcl-XL and/or Bcl-W and/or Bcl-2: Asp-Thr-Arg-Arg-Ser-Met-Val-Phe-Ala-Arg-His-Leu-Arg-Glu-Val-Gly-Asp-Glu-Phe-Arg-Ser-Arg (SEQ. ID. NO.1).

EXAMPLE 2

Validation of the Interaction Between the Peptide Described in Example 1 and Bcl-W and/or Bcl-XL and/or Bcl-2

1) GST "Pull-Down"

The interaction between the peptide obtained in Example 1 and Bcl-W and/or Bcl-XL and/or Bcl-2 is validated by measuring the shift in the interaction between a Bid protein having a "BH3" motif and the fusion protein GST-Bcl-XL, GST-Bcl-W or GST-Bcl-2.

a) Synthesis of Radiolabelled Bid

The labelled protein is obtained using the TNT Quick Master kit (Promega). Forty μl of TNT mixture are incubated for 90 minutes at 30° C. together with 2 μl (equivalent to 20 μCi) of $^{35}$S-methionine (Amersham), 1 μg of plasmid DNA coding for Bid and a sufficient amount of water to obtain a volume of 50 μl.

The number of fmoles/μl of radioactive protein produced is calculated on the basis of the number of methionines in the protein.

b) GST "Pull-Down"

Four fmoles of radioactive Bid protein are incubated at 4° C. for 3 hours together with 3 μg of the fusion protein glutathione-S-transferase-Bcl-XL (GST-Bcl-XL) or glutathione-S-transferase-Bcl-2 (GST-Bcl-2) or glutathione-S-transferase-Bcl-W (GST-Bcl-W) or GST alone in 300 μl of binding buffer (142 mM KCl, 5 mM $MgCl_2$, 10 mM Hepes buffer, 0.5 mM DTT, 1 mM EDTA, protease inhibitor, pH 7.4) and 0.4% Triton X100. Beads of "Glutathione Sepharose 4 Fast Flow" (Amersham) are washed 3 times in the binding buffer and resuspended in that buffer so as to obtain a 50% solution. 20 μl are added to each sample and incubated with rotation at 4° C. for 1 hour. The beads are then washed 3 times in the binding buffer, and then 25 μl of 2×SDS buffer, Laemmli (Sigma) are added. The samples are then held for 5 minutes at 95° C. and then applied to a 12% Tris-glycine gel (Invitrogen). After electrophoresis, the gel is subsequently incubated in a drying solution (Invitrogen) for 30 minutes and then dried for 150 minutes at 70° C. The radioactive proteins are revealed by exposure to a Kodak BioMax MS-1 film (Sigma). In order to carry out the competition test with the peptide under test, the latter is added to the initial solution in concentrations ranging from 5 to 20 μM.

c) Results

When the peptide obtained in Example 1 is added to the initial solution, the autoradiographic signal of Bid disappears. This result shows that the peptide obtained in Example 1 inhibits the interaction between Bcl-W and Bid, between Bcl-XL and Bid and between Bcl-2 and Bid.

By way of example, the result obtained between Bcl-XL and Bid is shown in FIG. 1.

2) Fluorescence Polarisation: Determination of the $K_d$ of the Interaction Between the Peptide Obtained in Example 1 and the Anti-Apoptotic Protein A 15 nM solution of the peptide obtained in Example 1 labelled with fluorescein at the N-terminal end is mixed with a solution containing the fusion protein GST-Bcl-XL or GST-Bcl-W at a concentration varying from 1 nM to 5 μM in a buffer containing $Na_2HPO_4$ 20 mM pH 7.4, EDTA 1 mM, NaCl 50 mM, pluronic acid F-68 0.05%. The fluorescence polarisation is then measured by the En Vision apparatus (Packard Perkin-Elmer).

The results obtained are shown in FIGS. 2 and 3.

Results: A significant increase in fluorescence polarisation is observed when the peptide obtained in Example 1 is incubated with the fusion proteins containing Bcl-XL and Bcl-W, demonstrating that it has been bound to these proteins.

The $K_d$ obtained with Bcl-XL is $2.15 \times 10^{-7}$M (FIG. 2) and that obtained with Bcl-W is $4.11 \times 10^{-7}$M (FIG. 3).

EXAMPLE 3

Screening Test for Compounds Capable of Inhibiting the Interaction Between Bcl-W and/or Bcl-Xl and/or Bcl-2 and the Peptide Obtained in Example 1

The compounds under test are dispensed into 384-well plates (Corning Flat Bottom) at a final concentration of 10 μg/ml. One well is filled with an equivalent amount of buffer/solvent without the compound under test to form the control. The peptide obtained in Example 1, labelled with fluorescein, is added to each well so as to obtain a final concentration of 15 nM. The fusion protein GST-Bcl-XL, GST-Bcl-W or GST-Bcl-2 is then added so as to obtain a final concentration of 500 nM (Bcl-XL, Bcl-2) and 1 μM (Bcl-W) in a buffer containing Na$_2$HPO$_4$ 20 mM pH 7.4, EDTA 1 mM, NaCl 50 mM and pluronic acid F-68 0.05%. The fluorescence polarisation is then measured by the En Vision apparatus (Packard Perkin-Elmer). A significant decrease in the fluorescence polarisation recorded in the test carried out with the test compound compared to that obtained without the test compound (control well) allows the conclusion that the compound possesses inhibitory activity. Conversely, a significant increase in fluorescence polarisation in the test with the test compound compared to the control allows the conclusion that the compound possesses activating activity.

The invention claimed is:

1. An isolated peptide consisting of the amino acid sequence set forth in SEQ ID NO:1 which interacts with an anti-apoptotic protein of the Bcl-2 family, wherein the anti-apoptotic protein of the Bcl-2 family is selected from the group consisting of Bcl-2, Bcl-XL and Bcl-W.

2. A nucleic acid sequence coding for the peptide of claim 1, consisting of the sequence set forth in SEQ ID NO:2.

3. A nucleic acid sequence deduced according to the genetic code from the amino acid sequence of claim 1.

4. A recombinant vector comprising the nucleic acid sequence set forth in SEQ ID NO:2, which is operably linked to regulatory elements for expression of the peptide of claim 1.

5. The recombinant vector of claim 4, which is a plasmid comprising the regulatory elements necessary for expression of the peptide in a host cell.

6. A host cell, which has been transformed with the recombinant vector of claim 4.

7. A method for identifying a compound which modifies the interaction between the peptide of claim 1 and an anti-apoptotic protein of the Bcl-2 family, wherein the antt-apoptotic protein of the Bcl-2 family is selected from the group consisting of Bcl-2, Bcl-XL and Bcl-W, comprising the following steps:
   a) fluorescently labelling the peptide of claim 1;
   b) incubating the labelled peptide in the presence or absence of a test compound;
   c) adding a fusion protein comprising an anti-apoptotic protein of the Bcl-2 family; and
   d) measuring the fluorescence polarisation.

8. A method for, identifying a compound which inhibits the interaction between the peptide of claim 1 and an anti-apoptotic protein of the Bcl-2 family, wherein the anti-apoptotic protein of the Bcl-2 family is selected from the group consisting of Bcl-2, Bcl-XL and Bcl-W, comprising the following steps:
   a) fluorescently labelling the peptide of claim 1;
   b) incubating the labelled pepticle in the presence or absence of a test compound;
   c) adding a fusion protein comprising an anti-apoptotic protein of the Bcl-2 family;
   d) measuring the fluorescence polarisation; and
   e) selecting a test compound for which the increase in fluorescence polansation observed with the test compound is significantly less than that observed without the test compound.

9. A method for identifying a compound which enhances the interaction between the peptide of claim 1 and an anti-apoptotic protein of the Bcl-2 family, wherein the anti-apoptotic protein of the Bcl-2 family is selected from the group consisting of Bcl-2, Bcl-XL and Bcl-W, comprising the following steps:
   a) fluorescently labelling the peptide of claim 1;
   b) incubating the labelled peptide in the presence or absence of a test compound;
   c) adding a fusion protein comprising an anti-apoptotic protein of the Bcl-2 family;
   d) measuring the fluorescence polarisation; and
   e) selecting a test compound for which the increase in fluorescence polarisation observed with the test compound is significantly greater than that observed without the test compound.

10. The method of claim 7, wherein the anti-apoptotic protein of the Bcl-2 family is Bcl-2.

11. The method of claim 7, wherein the anti-apoptotic protein of the Bcl-2 family is Bcl-XL.

12. The method of claim 7, wherein the anti-apoptotic protein of the Bcl-2 family is Bcl-W.

13. The method of claim 7, wherein the peptide is fluorescently labelled with fluorescein.

14. The method of claim 7, for identifying a compound to modulate apoptosis.

15. The method of claim 7, for identifying a compound for the treatment of autoimmune diseases, neurological disorders and cancers.

* * * * *

UNITED STATES PATENT AND TRADEMARK OFFICE
CERTIFICATE OF CORRECTION

PATENT NO. : 7,459,434 B2  
APPLICATION NO. : 10/566668  
DATED : December 2, 2008  
INVENTOR(S) : Olivier Geneste et al.

It is certified that error appears in the above-identified patent and that said Letters Patent is hereby corrected as shown below:

Title Page; item (73);  
Assignee: "Les Laboratories Servier" should be --Les Laboratoires Servier--.

Column 9, Line 22: "antt" should be --anti--.

Column 10, Line 5: "polansation" should be --polarisation--.

Signed and Sealed this

Twenty-first Day of April, 2009

JOHN DOLL  
*Acting Director of the United States Patent and Trademark Office*

```
SEQUENCE LISTING

<160> NUMBER OF SEQ ID NOS: 4

<210> SEQ ID NO 1
<211> LENGTH: 22
<212> TYPE: PRT
<213> ORGANISM: Homo sapiens

<400> SEQUENCE: 1

Asp Thr Arg Arg Ser Met Val Phe Ala Arg His Leu Arg Glu Val Gly
1               5                   10                  15

Asp Glu Phe Arg Ser Arg
            20

<210> SEQ ID NO 2
<211> LENGTH: 66
<212> TYPE: DNA
<213> ORGANISM: Homo sapiens

<400> SEQUENCE: 2
gatacccgtc gcagcatggt gtttgccagg cacctgcggg aggtgggaga cgagttcagg      60
agcaga                                                                66

<210> SEQ ID NO 3
<211> LENGTH: 19
<212> TYPE: DNA
<213> ORGANISM: Artificial
<220> FEATURE:
<223> OTHER INFORMATION: primer

<400> SEQUENCE: 3
gctttggaat cactacagg                                                  19

<210> SEQ ID NO 4
<211> LENGTH: 19
<212> TYPE: DNA
<213> ORGANISM: Artificial
<220> FEATURE:
<223> OTHER INFORMATION: primer

<400> SEQUENCE: 4
cacgatgcac gttgaagtg                                                  19
```